United States Patent [19]
Bona et al.

[11] Patent Number: 5,740,117
[45] Date of Patent: Apr. 14, 1998

[54] OPTICAL MEMORY FOR STORING DATA

[75] Inventors: Gian-Luca Bona, Hedingen; Roland Germann, Wangen; Huub Salemink, Adliswil, all of Switzerland

[73] Assignee: International Business Machines Corporation, Armonk, N.Y.

[21] Appl. No.: 793,763

[22] PCT Filed: Sep. 15, 1994

[86] PCT No.: PCT/EP94/03095

§ 371 Date: Feb. 27, 1997

§ 102(e) Date: Feb. 27, 1997

[87] PCT Pub. No.: WO96/08826

PCT Pub. Date: Mar. 21, 1996

[51] Int. Cl.$^6$ .................................................. G11C 19/30
[52] U.S. Cl. ........................................ 365/215; 365/106
[58] Field of Search .................................. 365/106, 215, 365/73, 114, 234

[56] References Cited

U.S. PATENT DOCUMENTS 4,877,952 10/1989 Halemane et al. ................. 365/106
5,058,060 10/1991 Su ............................................. 365/215

FOREIGN PATENT DOCUMENTS

0078140 5/1983 European Pat. Off. ............. 365/215

*Primary Examiner*—Son T. Dinh
*Attorney, Agent, or Firm*—Thomas R. Berthold

[57] ABSTRACT

The present invention concerns optical memories. Such an optical memory (30) comprises a data line (31) which is optically coupled via a directional waveguide coupler (33) to a circular memory loop (32). In addition, it comprises a pump line (35), which is employed in order to couple a refresh signal into the loop (32). As in case of the data line, the pump line is coupled via a directional waveguide coupler (34) to the loop (32). The counter propagating refresh light pulse provides for an amplification of the light pulse circulating in the memory loop being doped with Erbium ions. The length L of the memory loop (32) is chosen such that the circulation frequency of the light pulse in said loop (32) is equal to the clock frequency of the optical memory (30). The memory provides for individual manipulation of each stored optical bit.

17 Claims, 8 Drawing Sheets

OPTICAL MEMORY FOR STORING DATA

TECHNICAL FIELD

The present invention concerns an apparatus for storing light pulses in a small waveguide memory loop.

BACKGROUND OF THE INVENTION

Photon storage, in analogy to electron storage such as the well known capacitor memory cell, is very difficult because of the physical problem of containment of a photon or photon stream. Up to now, most approaches for storing photons are either based on the effect of optical bistability or on the utilization of long fiber loops.

Devices making use of the optical bistability are usually technologically complex and expensive. Much of the early work on optical bistability was motivated by the idea that optics could avoid some of the intrinsic speed limitations of electronic storage systems. The devices based on the effect of optical bistability rely on electro-optic conversion and hence an electron is stored in this case. A two-dimensional access or emitting function can be implemented with these kind of devices.

Figure 1:
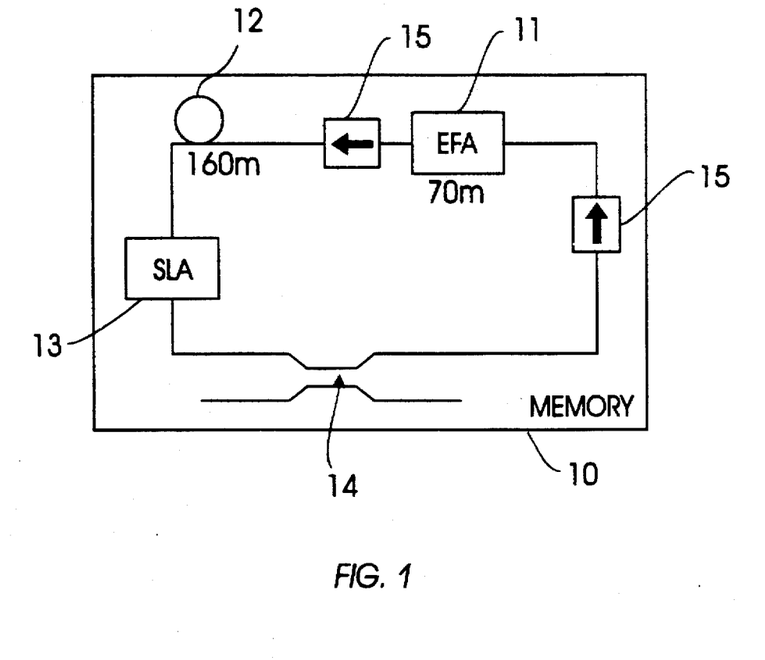
FIG. 1 shows a conventional recirculating fiber loop used for the delay and storage of a sequence of bits (background art).

Fiber loops exist in the form of sequential storage pipes, where a photon stream, e.g. a sequence of light pulses, flows or recirculates in a first-in first-out (FIFO) fashion. These fiber loops are used as optical delay lines, but do not allow a random-access to the light pulses circulating in such a loop. A typical photon memory device based on a recirculating fiber loop is described in "Programmable Photonic Fiber Loop Memory", A. Dickson et al., Proceedings of the 16th Australian Conference on Optical Future Technology, p. 274–277, 1991. A typical recirculating fiber loop memory 10 is illustrated in FIG. 1. This memory 10 consists of a directional coupler 14 for coupling light into it. This memory 10 comprises an Erbium doped fiber amplifier (EFA) 11 with a 70 meters long $Er^+$-fiber, a fiber loop 12 (fiber coil) which is 160 meters long, a semiconductor laser amplifier (SLA) 13 operating as optical switch, and two optical isolators 15, each being depicted as box with a black arrow. These kind of devices are bulky and expensive.

For future functions in optical processing and data communication it is desirable to have a photon storage device in much analogy to a conventional electronic cache memory, i.e. there is a great demand for an optical memory being as easy to use as their electronic counterparts. These kind of devices will most likely be used in many fields of photonics, including telecommunications, packet switching, and optical computing. Usage of an optical memory is foreseen in bit-selective manipulation at high data rates (e.g. 10 Gb/sec), like processing, temporal storage and recognition. It is very important for such a device, that it is capable of storing and manipulating optical bits individually. Ideally it should be integrable to optically perform elemental logical functions. Any conversion of photons into electrons and vice versa should be avoided in order to increase efficiency and to minimize access time to data stored.

SUMMARY OF THE INVENTION

It is an object of the present invention to provide an apparatus for optically storing light pulses carrying information.

It is another object of the present invention to provide an apparatus for optically storing light pulses carrying information such that each light pulse stored is individually addressable.

The above objects have been accomplished by provision of memory cells comprising a data line, a directional waveguide coupler which can be switched from a 'bar-state' to a 'cross-state', and a circular waveguide memory loop for storing a light pulse circulating therein, the data line being optically coupled via the directional waveguide coupler to the loop such that a light pulse on the data line is coupled into said memory loop if the directional waveguide coupler is in the 'cross-state', or passes the directional waveguide coupler—without being coupled into said memory loop—if it is in the 'bar-state'. The length L of said memory loop is chosen such that the circulation frequency of said light pulse in the memory loop is equal to the clock frequency of said optical memory.

DESCRIPTION OF THE DRAWINGS AND NOTATIONS USED

The invention is described in detail below with reference to the following schematic drawings.

GENERAL DESCRIPTION

For the sake of simplicity, it is assumed in the following, that a light pulse represents-one bit of information. This is not necessarily so, but for most applications this approach is reasonable.

Figure 2:
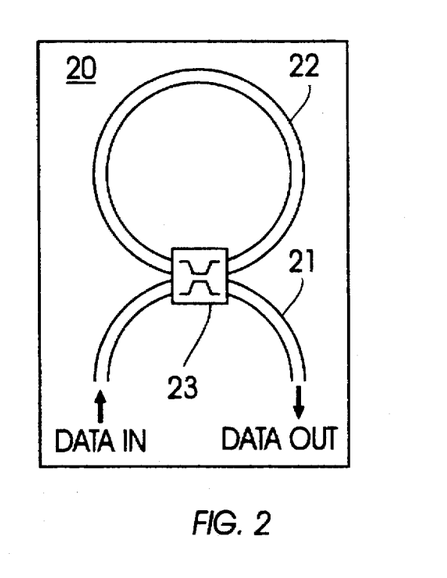
FIG. 2 shows an optical random-access memory according to the present invention.

The present invention will be described in more detail in connection with an optical memory consisting of a single bit memory cell 20 only, as illustrated in FIG. 2. This memory cell 20 at least comprises a circular memory loop 22, a directional waveguide coupler 23, and a data line 21. These basic elements are arranged such that a light pulse can be fed via said data line 21 and said directional waveguide coupler 23 into said memory loop 22. The directional waveguide coupler 23 can be electrically or optically addressed in order to switch from a so-called 'bar-state' to a 'cross-state'. If the directional waveguide coupler 23 is in the 'bar-state', the light pulse passes the loop 22 without being coupled into it. If the coupler 23 is in the 'cross-state', the light pulse is coupled into the loop 22. Switching between these two states facilitates selective storage of light pulses in said memory loop 22. A light pulse being coupled into this loop 22 circulates therein. The duration of this circulation is limited due to waveguide propagation losses in the loop. These losses are caused mainly by the waveguide material as such and by bending loses depending on the particular geometry of the loop.

Details on directional waveguide couplers are for example described in the book "An Introduction to Photonic Switching Fabrics", H. S. Hinton, Plenum Press, New York and London, 1993. Further details are disclosed in "Optical Switching Expands Communications-Network Capacity", W. H. Nelson et al., Laser Focus World, June 1994, pp. S17–S20. For sake of convenience, directional waveguide couplers are depicted in the Figures as a simple box carrying a symbol meant to represent two waveguides with a narrow section. In this narrow section, the energy is coupled from the first waveguide into the second one, depending on the state ('cross'- or 'bar-state') of the coupler. A classification of such couplers is given in the following.

Basic categories of waveguide couplers:
1. Interference based couplers, utilizing the optical interference caused by a phase difference in two arms of the waveguide coupler. The phase difference can for example be introduced by electro-, acousto-, or thermo-optic effects.
2. Internal reflection optical couplers, relying on a (total) internal reflection principle inside the waveguide structure. The internal reflection zone acts as a mirror and can for example be introduced as a refractive index change into the waveguide by carrier injection via electrodes. Details are for example given in "InGaAsP/InP optical Switches Using Carrier Induced Refractive Index Change", K. Ishida et al., Applied Physics Letters, Vol. 50, No. 3, pp. 141–142, 1987.
3. Gain/Absorption couplers, in the shape of a waveguide tree or Y-branch with a 3 dB splitting ratio and optical gain sections in both legs. Details are for example given in "Integrated Lossless InP/InGaAsP 1 to 4 Optical Switch", Davies et al., Electronics Letters, Vol. 28, No. 16, pp. 1521–1522, 1992. The switch function uses two effects: (i) in the switched leg, optical gain is provided to raise the optical intensity to the required (original) intensity and (ii) in the non-switched leg, the optical signal undergoes a well defined attenuation via the absorption loss and hence a certain extinction ratio with respect to the switched channel (i) is obtained.
4. Modal evolution couplers, where the propagation or attenuation of a desired optical mode is given by the matching of the modes in the respective waveguide branches. Such matching is accomplished by the waveguide design and can for example be influenced by the electro-optic effect using electrodes. Details are given in "Digital Optical Switch", Y. Silberberg et al., Applied Physics Letters, Vol. 51, No. 16, pp. 1230–1232, 1987.
5. All-optical couplers: in this category, non-linear optical effects like the refractive-index changes are induced by strong optical intensities. Examples are the optical Kerr effect, Sagnac-type interferometer couplers like the nonlinear optical loop mirror (NOLM), and four-wave mixing.

Such directional waveguide couplers, which are either electrically or optically addressable as described above, and clocked at the appropriate rate, are well suited for use in the systems herein described.

Figure 3A:
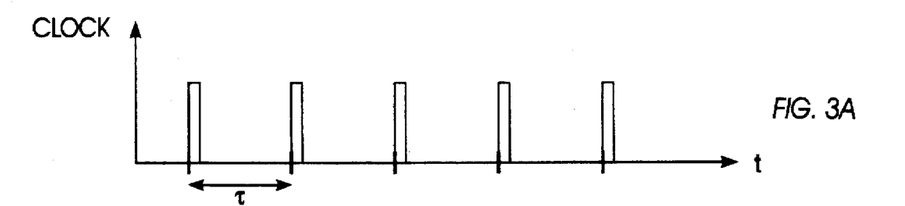
FIG. 3A is a timing diagram of the clock signal of an optical memory in accordance with the present invention.
Figure 3B:
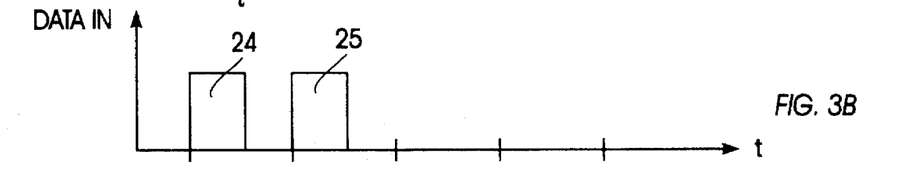
FIG. 3B is a timing diagram of the data signals on the data line of an optical memory in accordance with the present invention.
Figure 3C:
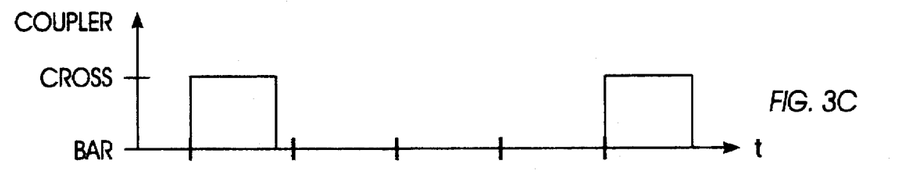
FIG. 3C is a timing diagram showing the status of the directional waveguide coupler of an optical memory in accordance with the present invention.
Figure 3D:
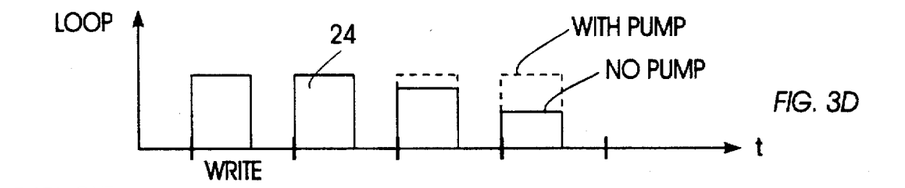
FIG. 3D is a timing diagram showing the intensity of a light pulse circulating in the waveguide loop of an optical memory in accordance with the present invention.
Figure 3E:
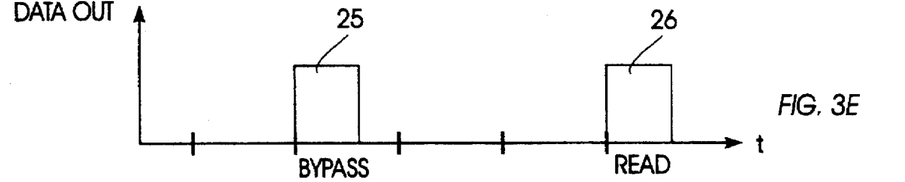
FIG. 3E is a timing diagram showing the data output signals on the data line of an optical memory in accordance with the present invention.
Figure 3F:
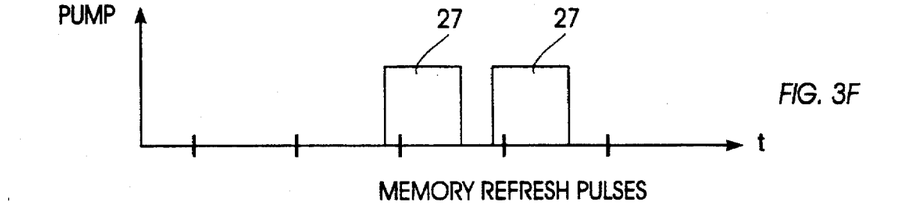
FIG. 3F is a timing diagram showing suitable pump pulses for refresh of the light pulse circulating in the waveguide loop of an optical memory in accordance with the present invention.

In order to allow random-access to a bit stored by means of a light pulse circulating in such a memory loop, its position within the loop must be predictable, and the circulation frequency of the light pulse has to be equal to the clock frequency which is defined by the environment in which said memory is used. This facilitates random-access to the data stored. The design of the waveguide loop has to be such that the circulation frequency matches the clock frequency defined by the unit which requests retrieval of data and which needs these data for further processing. The basic principle of the present invention is described in the following in connection with FIGS. 3A–3F. In FIG. 3A, the system clock, i.e. the clock signal applied to the present optical memory, is illustrated. A clock cycle (timing clock period) is denoted by τ. Two light pulses 24 and 25, FIG. 3B, are fed via the data line 21 to the optical memory. The first pulse 24 is coupled into the loop 22 since the directional waveguide coupler 23 is in the 'cross-state', see FIG. 3C, whereas the second pulse 25 is bypassed (coupler in 'bar-state'). The light pulse being coupled into the loop 23 now circulates in it, as indicated in FIG. 3D, an passes the directional waveguide coupler each time when a clock signal is applied. The length L of the loop 22 is in the present example chosen such that the pulse circulation time in the loop is equal to τ, i.e. L=τc/n, where c is the free-space speed of light, and n is the refractive index of the waveguide material in said circular memory loop 22.

the beginning of each clock cycle, the pulse in the loop passes the directional waveguide coupler 23. If no pump pulse is applied to the loop, the signal is attenuated, i.e. the amplitude decreases with time, as illustrated in FIG. 3D by fully drawn boxes. With adequate pump pulse the signal strength is held constant, as indicated by the dashed boxes in lo FIG. 3D. The light pulse 25 has not been coupled into the loop and passes the coupler 23 as shown in FIG. 3E. The light pulse circulating in the loop 22 is read out if the coupler is switched from 'bar-state' into 'cross-state', as indicated in FIG. 3C. This pulse then appears on the data line 21 (see pulse 26 in FIG. 3E). Appropriate pump pulse signals 27 are shown in FIG. 3F. These pump signals, if properly synchronized with respect to the stored (circulating) pulse, would restore the original signal strength in the loop.

At a given data rate b, the length 1 of an individual light pulse in space is given by l=c/nb, where c is the free-space speed of light, and n is the refractive index of the waveguide material in said circular memory loop 22. For a data rate b=10 Gb/s and a waveguide made of a compound semiconductor material like GaAs or InP with n=3.2, the optical pulse length within this waveguide loop is l=10 mm. The circumference L of the memory loop 22 is in the present example chosen to match this length l, i.e. the length L of the memory loop 22 is equal to the optical pulse length l. The resulting loop radius r=(1/2 π)(c/nb) is 1.5 mm. It has been found that this value for the radius r is still a factor of ten above the waveguide radius where the excess bending loss becomes important. Details on bends in optical ridge waveguides are given in the Ph.D. thesis of E. C. M. Pennings with title "Bends in Optical Ridge Waveguides; Modelling and Experiments", Technical University of Delft, The Netherlands, 1990, p. 138. Excess bending losses seem to play an important role if the radius is smaller than 0.15 mm.

In the cell design, the waveguide propagation loss of <0.7 dB/cm is herein used to a first approximation. The losses in the memory loop 22 define the storage lifetime of a circulating pulse. If the signal to noise (S/N) ratio is too small, the light pulse can not longer be detected, i.e. retrieved, since due to the waveguide and propagation losses, the optical bit intensity will be attenuated to a level below detection threshold.

In the above example, the directional waveguide coupler 23 is used for selectively coupling a light pulse into the memory loop 22. The same directional waveguide coupler 23 can be used for retrieving a bit which is stored as circulating light pulse. If the directional waveguide coupler 23 is switched from the 'bar-state' to the 'cross-state', the light pulse is coupled back into the data line 21. The data line for feeding data to said coupler might be the same as the one used for retrieval of data, as illustrated in FIG. 2. Another embodiment is conceivable where there are two separate lines for storage and retrieval.

For some applications, it is sufficient to employ such a single bit memory cell as illustrated in FIG. 2, in which the light pulse is only stored for a fraction of a second. Depending on the design, material and radius of such a memory loop, the above mentioned waveguide loss allows a number of approximately 10 loop circulations, which is equal to 10 clock periods. Such single bit memory cells might be used for synchronization purposes, or as buffers in optical switch fabrics.

In order to obtain an optical memory suited for long-term storage of a bit, the light pulse circulating in the memory loop needs a refresh. This concept is similar to the one of conventional dynamic random-access memories which require a dynamic refresh in order to keep the information stored. If the light pulse is amplified, it can be stored for an arbitrary time interval to allow functions like buffering or additional processing. A dynamic random-access optical memory 30, in accordance with the present invention, is described in connection with FIG. 4A. This optical memory 30, comprises a data line 31 which is optically coupled via a directional waveguide coupler 33 to a circular memory loop 32. In addition, it comprises a pump line 35, which is employed in order to couple a refresh signal into said memory loop 32. As in case of the data line, the pump line 35 is coupled via a directional waveguide coupler 34 to said loop 32. The counter propagating refresh light pulse provides for an amplification of the light pulse circulating in the memory loop, if said memory loop is doped with Erbium ions. These Erbium ions provide for optical gain which compensates the waveguide losses when an optical pump pulse is fed into the loop, either in a direction against or with the signal stream (counter- or co-propagation). As a simplified scheme it is assumed that the Erbium ions in the host matrix of the loop form a three-level energy system as described in "Design of 1480-nm diode-pumped $Er^{3+}$-doped integrated optical amplifiers", F. Horst et al., Optical and Quantum Electronics, Vol. 26, pp. S285–S299, 1994. The Erbium ions are transferred from their ground state to the highest excited state by the incident pump light; from this level the ions relax to the slightly lower lasing level. From this lasing level the ions can return into the ground state under emission of photons of equal energy as the propagating signal and thus amplify the circulating flux at the signal wavelength (or energy). Under unpumped conditions, the optical bit that is circulating in the loop will gradually be attenuated, whereas upon optical pumping of the Erbium ions in the loop the intensity of this optical bit will be amplified and can be restored. For completeness it has to be noted that the energy levels mentioned above are actually somewhat broadened energy bands and that the above mentioned transitions take place between initial and final states within these bands: this allows to use an energy window for lasing action instead of just a single line. Further details on this physical effect are given in "The Golden Age of Optical Fiber Amplifiers", E. Desurvire, Physics Today, American Institute of Physics, pp. 20–27, January 1994.

This mechanism of amplification is described here for the example of Erbium ions as amplifying medium as commonly used today in the 1,55 μm data and telecommunication window. However, it should be noted that any amplifying element either optically or electrically pumped has the same effect. In particular the refresh of data light pulses is not restricted to a specific optical wavelength.

Figure 4A:
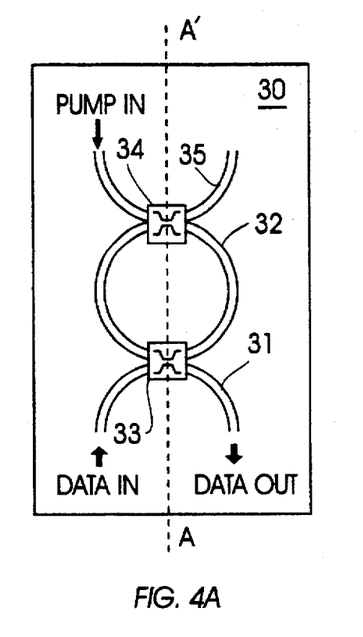
FIG. 4A shows an optical memory cell, according to the present invention, which has a separate pump line with active directional waveguide coupler.

In the present example, this directional waveguide coupler 34 can be switched from 'bar-state' to 'cross-state' such that one can select whether a refresh pulse is to be coupled into the loop 32 or not. If the information, i.e. the light pulse, stored in said loop is not longer needed, the directional waveguide coupler 34 can be blocked such that no refresh signal goes into the loop. In this case no active reset is necessary since the light pulse disappears within a fraction of a second. Further, unpumped $Er^+$-ions act as absorbers for light in the 1,55 μm range.

Figure 4B:
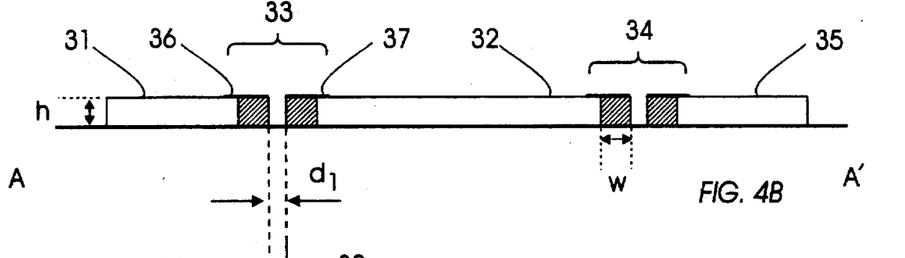
FIG.4B is a schematic, cross-sectional view of the memory cell shown in FIG. 4A.
Figure 4C:
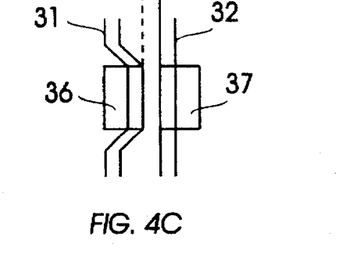
FIG. 4C is a sketch of the directional coupler of the memory cell shown in FIG. 4A.

A cross-sectional view of the dynamic random-access optical memory 30 is shown in FIG. 4B. The waveguide layer has a height h and the waveguides have a width w. The height is for example 3–5 μm and the width between 5 and 10 μm. The directional waveguide coupler 33 comprises a narrow section where the data line 31 approaches the circular waveguide loop 32. The coupler separation $d_1$ of the coupler, i.e. the distance between data line 31 and loop 32, is typically between 0,2 and 0,4 μm. In the embodiment illustrated in FIG. 4, the directional couplers 33 and 34 have electrical control inputs. A simplified top view of the coupler 33 is shown in FIG. 4C. The control input, basically comprising two metal electrodes 36 and 37, is electrical and has the capability of switching the coupler from the 'bar-state' to the 'cross-state'.

In order to allow a refresh by means of a counter propagating and/or co-propagating pump pulse, the memory loop has to be doped (at least partially) with Erbium ions, or with an appropriate amplifying medium as described above.

Figure 14:
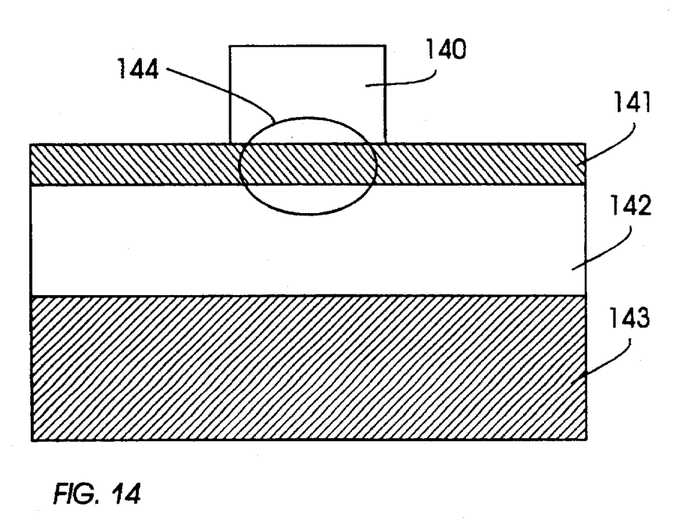
FIG. 14 is a schematic, cross-sectional view of of a stripe-loaded waveguide structure.

Different kind of waveguide structures are known in the art. Typical structures are called stripe-loaded waveguide, buried channel waveguide, rib waveguide, embedded stripe waveguide, and ridge waveguide, just to name some of the well known structures. In the; present description and Figures only rib or ridge waveguide structures are shown for sake of simplicity. All other kinds of waveguide structures are as well suited. A typical example of a waveguide structure being suited for use in connection with the present invention is given in FIG. 14. In this Figure, a cross-sectional view of a stripe-loaded waveguide is shown. This structure is grown on a substrate 143 and comprises a first InP layer 142 with lower refractive index n than the one of the InGaAsP waveguide layer 141 on top of it. Lateral confinement of the light wave in said waveguide 141 is achieved by means of an InP ridge 140 ('stripe') situated on top of the waveguide layer 141. Due to this loaded stripe, the light wave is confined as indicated by means of an ellipse 144. In another embodiment layer 142 and ridge 140 may consist of $SiO_2$, whereas the waveguide 141 as such comprises silicon oxynitride, hereinafter denoted as SiON. Details on this and other structures and materials of waveguides and the fabrication techniques thereof are for example given in a book titled "Guided-Wave Optoelectronics", edited by Th. Tamir, Springer-company, or in a book with title "Integrated Optics: Theory and Technology", R. G. Hunsperger, Second Edition, Springer Series in Optical Science Vol. 33, 1985. Typical waveguide materials are III/V materials like AlGaAs or InGaAsP, glasses, silica, SiON, as well as polymer films.

Figure 5A:
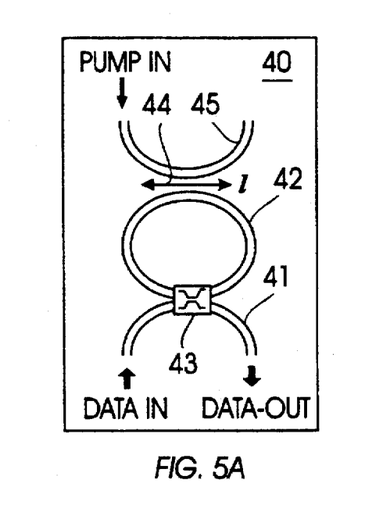
FIG. 5A shows an optical memory cell, according to the present invention, which has a separate pump line coupled via a passive directional waveguide coupler to the loop.
Figure 5B:
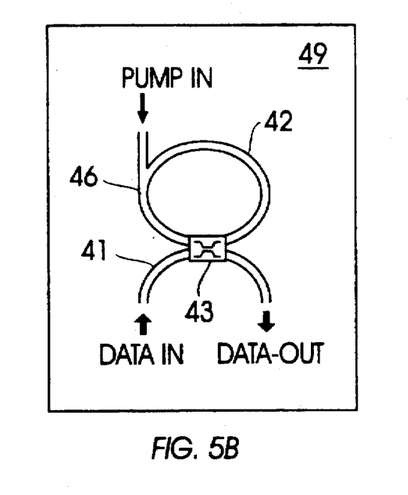
FIG. 5B shows an optical memory cell, according to the present invention, which has a separate pump line coupled via a Y-branch to the loop.
Figure 5C:
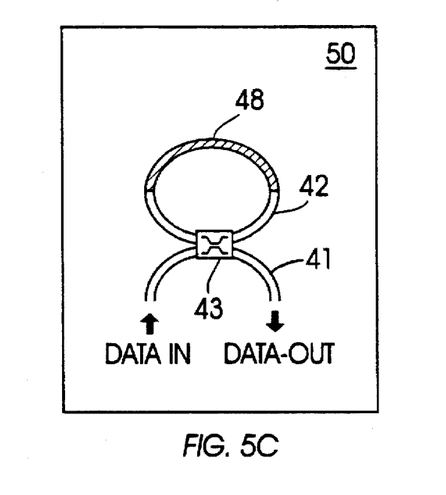
FIG. 5C shows an optical memory cell, according to the present invention, which comprises an semiconductor amplifying region.

Further embodiments of the present invention are given in FIGS. 5A–5C. By means of these Figures, different configurations are described which allow the refresh of a stored bit. Each of these systems comprises a data line 41, a directional waveguide coupler 43, and a memory loop 42. In the optical memory 40, shown in FIG. 5A, a passive directional waveguide coupler 44 with interaction length l is employed. The geometry and the distance between the pump line 45 and the memory loop 42 is chosen such that pad of the electro-magnetic wave which propagates in said pump line 45, is automatically coupled into the loop 42 which is doped with Erbium ions. In the next embodiment, illustrated in FIG. 5B, an optical memory 49 with separate pump line 46 is employed in order to feed the refresh light pulse into the loop 42. This pump line 46 is coupled by means of a Y-branch to the loop 42. The optical memory 50, which is illustrated in FIG. 5C, comprises an active semiconductor waveguide region 48 being integrated into said memory loop 42. This active region is employed to amplify the light pulse circulating in the loop 42 each time when it passes the active region 48, or each time when a refresh is required. By incorporating such a semiconductor optical amplifier into the loop, a pump line is not required, but electrical access is necessary. Details on such semiconductor optical amplifiers are for example given in "Random Access Fiber Loop Optical Memory With Active Switching and Amplifying Elements for Optical ATM Systems", R. Ludwig et al., proceedings ECOC (European conference on optical communication), Paris Sep. 9–12, 1991, Vol. 1, MoC2–4, pp. 101–104.

The pump light may be delivered continuously, or in a pulsed manner. The continuously delivered pump light has the advantage that there is no need for synchronization of a pump pulse with the light pulse circulating in a memory loop, if the respective directional waveguide coupler is synchronized, respectively. The pump light could also be supplied selectively, either in a periodically clocked way, or with an arbitrary time pattern.

Figure 6:
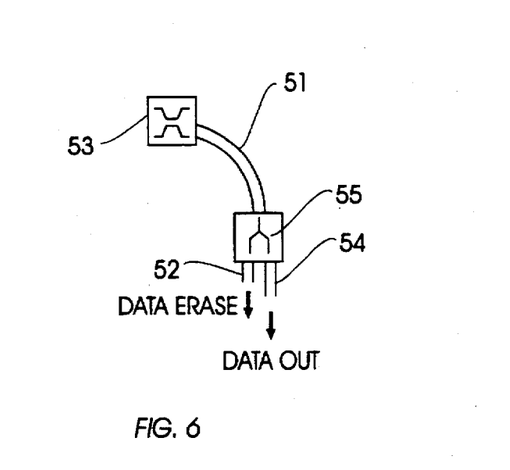
FIG. 6 shows a set-up which allows to erase data bits.

In order to reset an optical storage in accordance with the present invention, it is necessary either 1. to actively suppress the light pulse circulating in the memory loop by actively switching a pad of the loop to a higher absorption level,
2. to wait till a circulating light pulse disappeared due to losses (note: unpumped $Er^+$-ions show absorption), i.e. until the optical bit intensity drops below a certain decision level, or
3. to couple the light pulse out of the loop and to erase it. Active suppression of the light pulse is possible in that the bandgap is actively changed, e.g. using the quantum confined Stark effect, or by actively increasing the losses in the waveguide. This can be done thermally, or by carrier injection, i.e. by modification of the refractive index n of the waveguide. Passive suppression is obtained by means of $Er^+$-ions in the ground state (unpumped ions) which cause absorption in the waveguide. The absorption function could also be integrated into one of the directional waveguide couplers, which would eventually reduce the number of contact metallizations needed. If one takes the light pulse via a directional waveguide coupler out of the loop, the loop is reset and can be used for storage of the next information. The light pulse which has been taken out of the loop by means of a directional waveguide coupler 53 can be erased in the data line 51 as illustrated in FIG. 6. In this example, an active Y-branch is employed, which allows to couple this pulse in an erase line 52 (dump waveguide). Information which is not to be erased, is coupled in the the data output line 54.

Hereinabove, only single bit memory cells of different design and structure have been addressed. In order to obtain an optical storage register which is several bits wide, such single bit memory cells have to be arranged in an appropriate manner. Depending on the degree of integration, the particular arrangement of cells, the organization of write access, retrieval, refresh and reset, different optical memories can be obtained.

Figure 7:
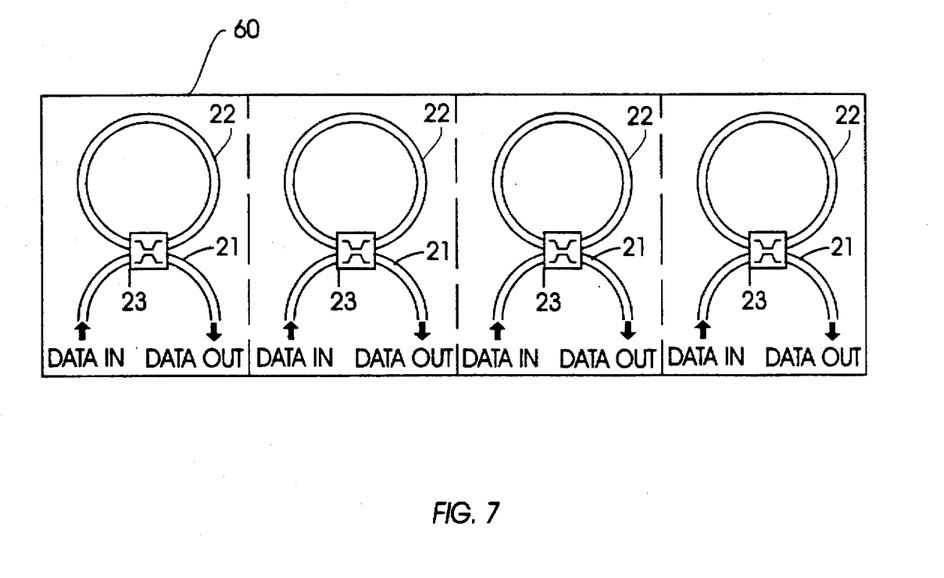
FIG. 7 shows a 4-bit wide random-access optical memory, according to the present invention, which has four individual input and output lines.

A first embodiment of a 4-bit optical random-access memory 60 is described in connection with FIG. 7. This is the most simple arrangement conceivable. Each single memory cell comprises a data line 21, a birectional waveguide coupler 23, and a circular waveguide loop 22. Such a 4-bit memory 60 has four individual input and output lines. Each memory cell can be viewed as separate and independent 1-bit memory. The greatest degree of flexibility is given if each memory cell is triggered by its own control signal. A first degree of simplification (level of integration) can be achieved in that one control signal is used to trigger all cells. The latter approach allows storage of four parallel bits at once, i.e. with one control pulse applied to the directional couplers 23.

Figure 8:
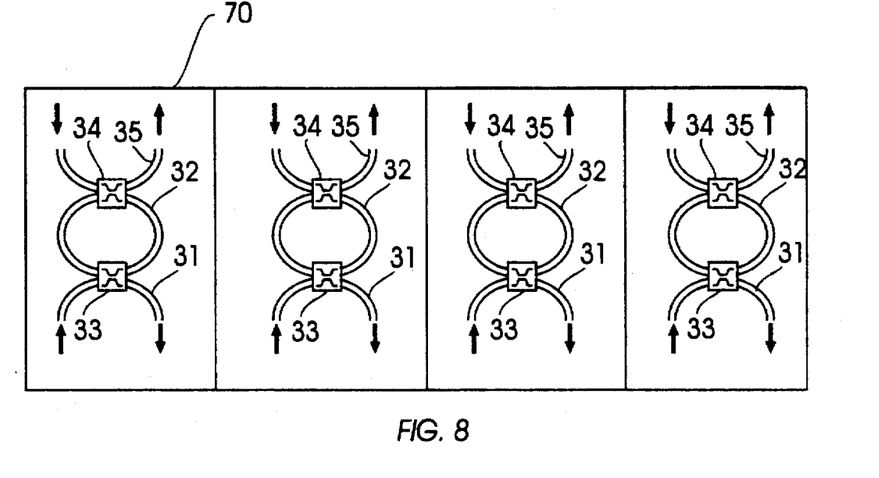
FIG. 8 shows a 4-bit wide random-access optical memory, according to the present invention, which has four individual input and output lines and four individual, separate pump lines.

Another embodiment is illustrated in FIG. 8. In this Figure, a 4-bit optical random-access memory 70 is shown which basically consists of single memory cells, as described in connection with FIG. 4A. Each memory cell has its own data line 31, directional couplers 33 and 34, circular waveguide loop 32, and pump line 35. Again, different control schemes with separate and/or common timing below the clock frequency are conceivable. These kind of 4-bit optical memories have four data inputs and outputs, as well as four pump signal inputs and outputs.

Figure 9:
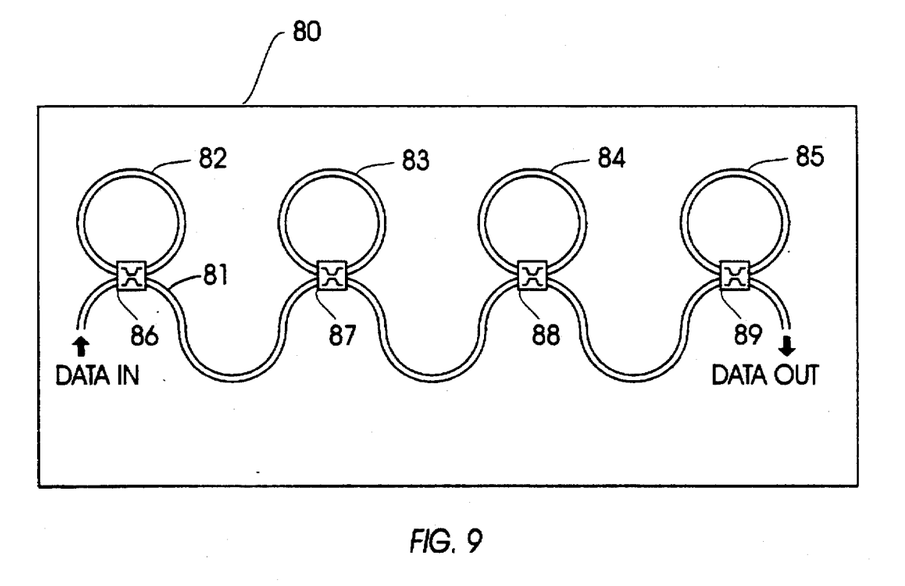
FIG. 9 shows a 4-bit wide random-access optical memory, according to the present invention, which has one common data line linking the memory loops in a serial manner.

A further embodiment of the present invention is illustrated in FIG. 9. Shown is a 4-bit optical memory 80 having one common data line 81, four memory loops 82 through 85 and directional waveguide couplers 86–89. A four bit sequence, for instance, which is fed via said data line 81 to this memory 80, can be stored bit-by-bit in the memory loops 82–85. The whole sequence of four bits, or pad thereof, can be retrieved and fed back into the common data line 81.

Figure 10:
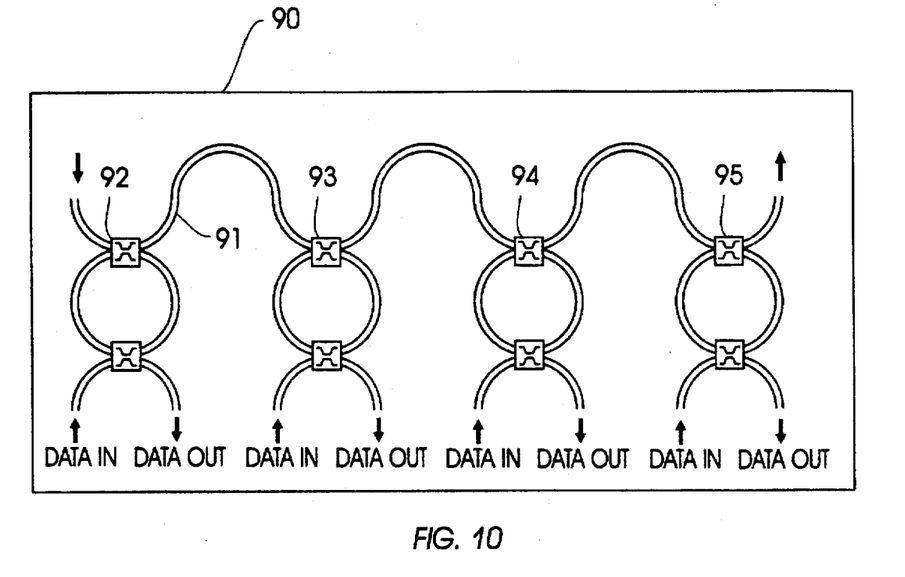
FIG. 10 shows a 4-bit wide random-access optical memory, according to the present invention, which has four individual input and output lines and one common pump line.

Another 4-bit optical random-access memory 90 is shown in FIG. 10. This memory comprises separate data lines for each single bit memory cell and a common pump line 91 which is employed to refresh the data stored from time to time. This pump line 91 is optically coupled via directional waveguide couplers 92–95 to the memory loops and the loops are sequentially pumped. An equalization of the pumping level is achieved by directional couplers with different coupling fractions, i.e. In the present embodiment the coupling fraction of directional waveguide coupler 95 might be higher than the one of coupler 92, to compensate the depletion of the pump power.

Figure 11:
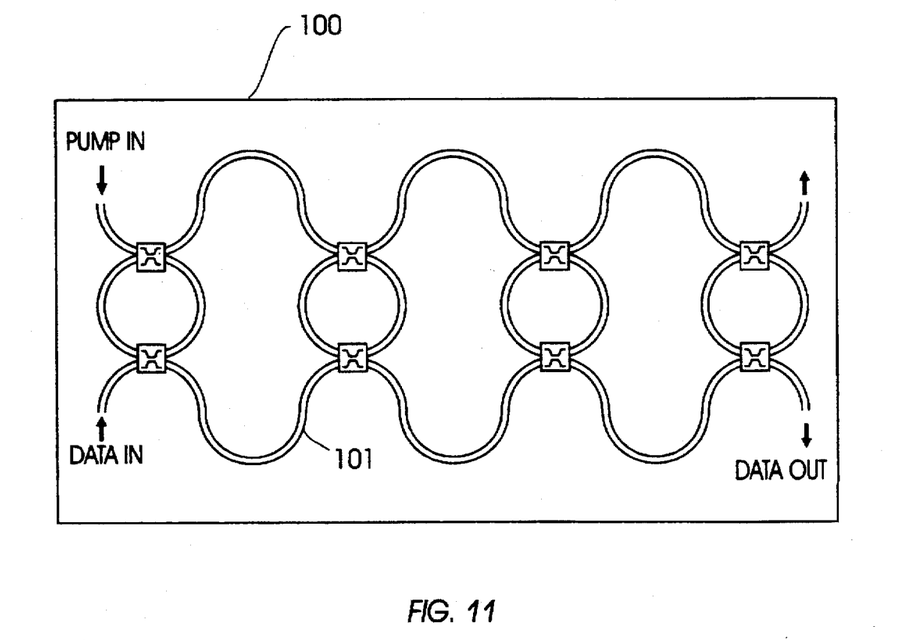
FIG. 11 shows a 4-bit wide random-access optical memory, according to the present invention, which has one common data line and one common pump line.
Figure 12:
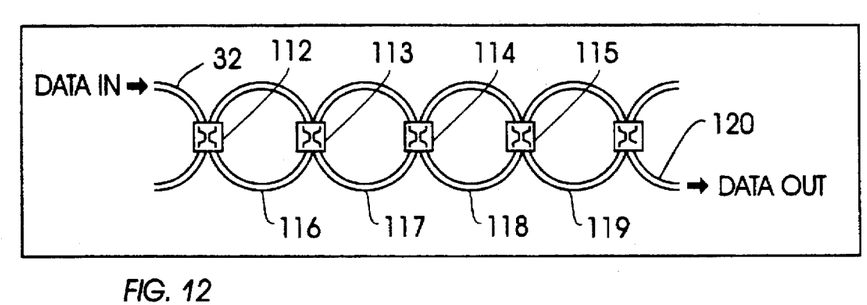
FIG. 12 shows a 4-bit wide FIFO type of optical memory.

In. FIG. 11, an embodiment is shown, which is a combination of the devices shown in FIGS. 9 and 10. The layout of the pump line of the 4-bit memories 90 and 100 allow some flexibility in pump-economics and usage of real-estate. Also it points to the usage of distributed pump sources.

Figure 13:
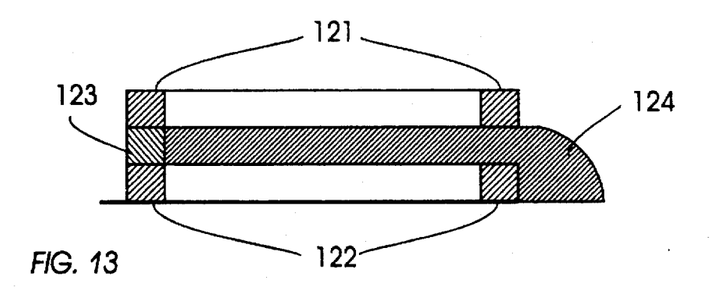
FIG. 13 is a schematic, cross-sectional view of two memory loops stacked on top of each other.

As the above described optical memories are essentially planar, more of such planar waveguide circuitry can be stacked vertically either by fabrication or by mounting. This leads to higher storage densities and allows to perform more advanced all-optical processing and switching by employing optical signals in the direction normal to the planar waveguides. A cross-sectional view of an exemplary embodiment is given in FIG. 13. In this Figure, two circular waveguide loops 121 and 122 are shown which are stacked on each other. On the right hand side both loops are separated by a spacer 124. On the left hand side, a grating coupler 123 is located between the lower loop 122 and the upper loop 121. The grating coupler 123 is employed to couple light out of the lower loop into the upper one.

Depending on the environment in which the present optical memories are used, there is no need for directional couplers that can be actively switched from 'bar-state' to 'cross-state'. Simple passive directional couplers might be used in case where each light pulse which passes such a coupler shall be coupled automatically into the loop. The arrangement of the directional couplers in said loops, the data coupler at one end and the pump coupler at the opposite end, is not mandatory. There are many different arrangements conceivable that provide for a high degree of flexibility when designing optical memories in accordance with the present invention.

What is claimed is:

1. Random-access optical memory (20) with a plurality of memory cells each comprising a data line (21), an active waveguide coupler (23) which can be switched from a first state to a second state, and a closed waveguide memory loop (22) for storing a light pulse (24) circulating therein, said data line (21) being optically coupled via said active waveguide coupler (23) to said memory loop (22) such that a light pulse (24) on said data line (21) is coupled into said memory loop (22) if the active waveguide coupler (23) is in the first state, or passes the active waveguide coupler (23), without being coupled into said memory loop (22), if it is in the second state, the length L of said memory loop (22) being such that the circulation frequency of said light pulse (24) in said memory loop (22) is equal to the clock frequency at which said optical memory (20) is designed to be operated.

2. The optical memory (20) of claim 1, wherein said memory loop (22), waveguide coupler (23) and data line (21) are integrated on the same substrate.

3. The optical memory (20) of the claims 1 or 2, wherein said light pulse (24) represents one bit.

4. The optical memory (20) of claim 1, wherein said waveguide coupler is a directional waveguide coupler (23) which can be electrically or optically addressed in order to switch from the first state ('bar-state') to the second stale ('cross-state') and vice versa to selectively couple light pulses from said data line (21) into said memory loop (22).

5. The optical memory (20) of the claims 1 or 4, wherein said waveguide coupler (23) is used not only for coupling a light pulse into said memory loop (22), but also for coupling a light pulse which circulates therein back into said data line (21).

6. The optical memory (60, 70, 90; 80, 100) of any of the preceding claims, comprising at least two memory cells, the data lines (21, 31) of each memory cell being either independently accessible, or the data lines of each memory cell being linked to each other in a serial manner in order to form one common data line (81; 91; 101).

7. The optical memory (30; 40; 49; 50) of any of the preceding claims, wherein means (44, 45; 46; 48) are provided for refresh of the light pulse circulating in said memory loop (32; 42).

8. The optical memory (30) of claim 7, wherein the refresh of the light pulse circulating in said memory loop (32) is achieved by means of a pump light pulse being fed via a pump line (35) into said memory loop (32) which is at least partially doped with Erbium ions, part of these Erbium ions being transferred from a ground-state into an upper-level state by said pump light pulse such that the light pulse circulating in said memory loop (32) is amplified by interaction with the Erbium-ions being in an upper-level state when passing the section of the memory loop (32) which is partially doped with Erbium ions.

9. The optical memory (30; 40; 49) of claim 8, wherein said pump line (35; 45; 46) is coupled via a) an active directional waveguide coupler (34), or b) a passive directional waveguide coupler (44), or c) a Y-branch, to said memory loop (32; 42).

10. The optical memory (50) of claim 7, wherein the refresh of the light pulse circulating in said memory loop (42) is achieved by means of a semiconductor amplifier section (48) being integrated into said memory loop (42).

11. The optical memory of any of the preceding claims, comprising at least two memory cells which are stacked on top of each other.

12. The optical memory of any of the preceding claims, comprising III–V semiconductors, glasses, $SiO_2$ and SiON, or polymers.

13. The optical memory of claim 12, wherein the substrate (143) comprises InP, the waveguide (141) comprises InGaAsP, and the ridge (140) formed on top of the waveguide (141) comprises InP.

14. The optical memory of claim 12, wherein the substrate (143) comprises $SiO_2$, the waveguide (141) comprises SiON, and the ridge (140) formed on top of the waveguide (141) comprises $SiO_2$.

15. The optical memory of claim 12, wherein the substrate (143) comprises glass, the waveguide (141) comprises a polymer, and the ridge (140) formed on top of the waveguide (141) comprises another polymer with lower refractive index than the waveguide (141).

16. A switch fabric for use in an optical data communication system comprising an optical memory in accordance with any of the preceding claims.

17. A computer in which part of the data processing is done optically, comprising an optical memory in accordance with any of the claims 1–16.

* * * * *